United States Patent [19]

Hickey et al.

[11] Patent Number: 5,098,701
[45] Date of Patent: Mar. 24, 1992

[54] CROSSLINKED PYRIDINOMETHACRYLATE POLYMERS

[75] Inventors: Deirdre M. B. Hickey, Welwyn; David G. Cooper, Harlow, both of England

[73] Assignee: SmithKline & French Laboratories, Ltd., Welwyn Garden City, United Kingdom

[21] Appl. No.: 626,123

[22] Filed: Dec. 11, 1990

[30] Foreign Application Priority Data

Dec. 4, 1989 [GB] United Kingdom ............... 8928278

[51] Int. Cl.$^5$ .................... A61K 31/74; C08F 26/06
[52] U.S. Cl. ................................. 424/78.1; 526/265
[58] Field of Search ................ 424/78, 79; 526/265

[56] References Cited

U.S. PATENT DOCUMENTS

| | | | |
|---|---|---|---|
| 3,227,672 | 1/1966 | Fertig et al. | 526/265 |
| 3,898,088 | 8/1975 | Cohen et al. | 96/84 A |
| 4,198,395 | 4/1980 | De Simone | 424/79 |
| 4,205,152 | 5/1980 | Mizuguchi et al. | 526/265 |
| 4,210,612 | 7/1980 | Karrer | 526/265 |
| 4,265,879 | 5/1981 | Fields et al. | 424/78 |
| 4,294,949 | 10/1981 | Karrer | 526/265 |
| 4,311,799 | 1/1982 | Mikake et al. | 521/31 |
| 4,412,011 | 10/1983 | Kihara et al. | 424/79 |
| 4,510,128 | 4/1985 | Khanna | 424/79 |
| 4,523,128 | 7/1985 | Sheldon et al. | 424/78 |
| 4,721,666 | 1/1988 | Yamanouchi et al. | 430/213 |
| 4,798,870 | 1/1989 | Lyle et al. | 525/327.1 |

FOREIGN PATENT DOCUMENTS

| | | | |
|---|---|---|---|
| 0050347 | 4/1982 | European Pat. Off. | 424/78 |
| 929391 | 6/1963 | United Kingdom. | |
| 1286949 | 12/1969 | United Kingdom. | |
| 2026501 | 2/1980 | United Kingdom. | |

OTHER PUBLICATIONS

Walfish et al., Water, Air & Soil Pollution, 12: 447–484 (1979).
Carpov et al., J. Macromol. Sci. Chem. A22 (5–7): 907–929 (1985).
Takeuchi et al., Chem. Pharm. Bull., 32(3): 823–831 (1984).
Petrariu et al., Revue Roumaine de Chimie, 25: 145–154 (1980).
Wessling et al., Makromol. Chem., suppl. 10/11: 319–333 (1985).

Primary Examiner—Thurman K. Page
Assistant Examiner—Peter F. Kulkosky
Attorney, Agent, or Firm—Wayne J. Dustman; Stuart R. Suter; Edward T. Lentz

[57] ABSTRACT

Pyridiniomethacrylate polymers are described which are of use in the treatment of elevated serum cholesterol levels. A compound of the invention is cross-linked 3-(N-methyl-3-pyridinio)propyl methacrylate chloride.

5 Claims, No Drawings

CROSSLINKED PYRIDINOMETHACRYLATE POLYMERS

The present invention relates to novel anion exchange polymers, processes for their preparation, pharmaceutical compositions containing them and their use in the lowering of plasma cholesterol levels in humans.

Coronary Heart Disease (CHD) is one of the most serious health problems of contemporary society. Worldwide epidemiological studies have shown that the incidence of CHD is related to a number of independent risk factors, in particular, for example, high concentrations of serum cholesterol (hypercholesterolaemia). Such adverse factors lead to atherosclerosis, and ultimately, in severe cases, intermittent claudication, cerebrovascular insufficiency, thrombosis and cardiac arrest.

It is known that ion exchange polymers can be used as sequestering agents to bind bile acids and salts in the intestinal tract, forming complexes which are then excreted in the faeces. This sequestering leads to a decrease in the amount of bile acids returning to the liver via enterohepatic circulation. The synthesis of replacement bile acids from hepatic cholesterol depletes hepatic cholesterol, regulates hepatic LDL receptors and consequently reduces plasma cholesterol levels. Such sequestering polymers have been recognised as useful for the treatment of hypercholesterolaemia and it is now proven that reducing serum cholesterol with bile acid sequestrants has a beneficial effect on protecting against the occurrence of coronary heart disease.

One particular agent which is currently used to lower serum cholesterol levels in humans by binding bile acids in the intestinal tract is cholestyramine. Cholestyramine is a cross-linked anion exchange polystyrene polymer bearing an ionisable trimethylammonium group bound to the polymer backbone. However, the use of this agent is associated with a number of undesirable side-effects, for example, it is unpalatable and must be taken in high doses and causes, in some cases, bloating, constipation and other gut side-effects. Furthermore, its ability to bind bile acids is inefficient with respect to the amounts of resin which it is necessary to use (up to 36 g per person per day).

In addition, other polymers have been disclosed in the art as sequestering agents, in particular U.S. Pat. No. 3787474 discloses the use of polymers derived from acrylic monomers of structure $RCH=CHR^1A$ in which R is methyl or ethyl, $R^1$ is hydrogen or methyl and A is for example, $CO_2(CH_2)_2N(R^3)_2R^4X$ in which $R^3$ is methyl or ethyl, and $R^4$ is hydrogen, methyl or ethyl and X is $Cl^-$, $Br^-$, $I^-$ or $CH_3SO_3-$, cross-linked with methyl bisacrylamide or ethylene glycol bis methacrylate; U.S. Pat. No. 4393145 discloses further polymers derived from acrylic monomers cross-linked through divinyl benzene (10 to 12%), and SE 7906129 discloses acrylic polymers cross-linked by 10–12% of a divinyl cross-linking monomer. However, despite these disclosures, no such acrylic polymers are available for human use and there remains a need for effective bile acid sequestering agents which do not have the disadvantages associated with agents currently in use.

The present invention therefore provides in a first aspect, cross-linked polymers of structure (I)

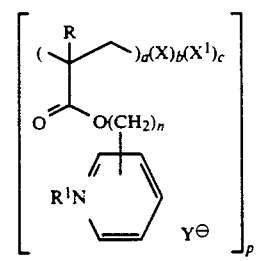

in which
a, b and c indicate the relative molar percentages of the units present in the polymer, (a) being from about 25 to about 99.5 molar percent, and (b) being from about 0.5 to about 8 molar percent;
X is a cross-linking unit;
$X^1$ is a comonomer unit;
R is hydrogen or $C_{1-4}$alkyl;
$R^1$ is $C_{1-20}$alkyl or $C_{1-20}$aralkyl;
n is 1 to 20;
p is a number indicating the degree of polymerisation of the polymer; and
$Y^-$ is a physiologically acceptable counter ion.

Suitably, (a) is from about 25 to about 99.5 molar percent; preferably from about 60 to about 99.5 molar percent.

Suitably, (b) is from about 0.5 to about 8 molar percent; preferably from about 0.5 to about 5.0 molar percent.

Suitably, X is a cross-linking unit i.e. a unit which provides a random distribution of cross-links between chains of polymers.

Preferred such units include, for example, divinylbenzene, alkylene glycol bis methacrylates of structure (i)

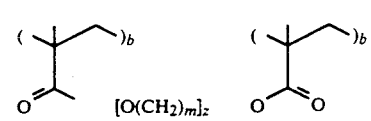

in which m is 2 to 6, z is 1 to 4 and (b) comprises from about 0.5 to about 8 molar percent of said polymer; and trismethacrylates of structure (ii)

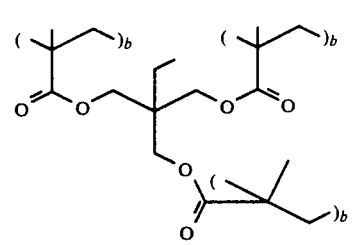

Suitably, z is 1 to 4, preferably z is 1. Suitably, m is 2 to 6, preferably m is 2.

Suitably $X^1$ is a comonomer unit. Preferably $X^1$ is styrene, an alkyl alkylate of structure (ii) or an alkylstyrene of structure (iii)

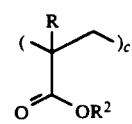

-continued

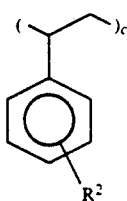

(iii)

in which R and c are as described for structure (I) and $R^2$ is $C_{1-20}$alkyl. In such comonomers groups R is preferably methyl and $R^2$ is preferably $C_{6-12}$alkyl.

Suitably $R^1$ is $C_{1-20}$alkyl or $C_{1-20}$aralkyl, preferably $C_{1-20}$alkyl, most preferably $C_{1-12}$alkyl.

Suitably, n is 1 to 20; preferably n is 1 to 10; most preferably n is i to 6.

p is a number indicating the degree of polymerisation of the polymer. Owing to the three dimensional cross-linkage, precise figures cannot be given for p, but in any case will be greater than 1,000.

Suitably $Y^-$ is a physiologically acceptable counter ion such as a bicarbonate, carbonate, formate, acetate, sulphonate, propionate, malonate, succinate, maleate, tartrate, citrate, maleate, fumarate, ascorbate, sulphate, phosphate, halide or glucuronate; or the anion of an amino acid such as aspartic or glutamic acid. Preferably $Y^-$ is a sulphate, phosphate or halide ion; more preferably a halide ion, in particular a chloride ion.

It is to be noted that $C_{1-4}$alkyl and $C_{1-20}$alkyl groups as herein defined include both straight and branched alkyl groups.

The polymers of the present invention are also characterised by their total exchange capacity i.e. the theoretical maximum capacity of the resin if each counter ion were to be exchanged with bile acid. In this specification the total exchange capacity is defined in terms of the number of milliequivalents of counter ion per gram of dry weight of polymer.

Suitable total exchange capacities are in the range of, for example where the counter ion $Y^-$ is chlorine, from about 1.5 to about 5.0 meq $Cl^-$ per gram of resin. Preferred within this range are polymers having a total exchange capacity of between 2 and 3 meq $Cl^-$/gram of resin.

It is to be noted that the term 'bile acid' when used herein shall be taken to include bile acids, bile salts and conjugates thereof.

The polymers of the present invention can be prepared by processes analogous to those known in the art. The present invention therefore provides, in a further aspect, a process for preparing the polymers of structure (I) which comprises alkylation of a polymer of structure (II)

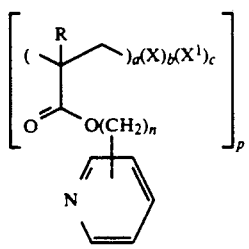

(II)

in which a, b, c, p, R, X, $X^1$ and n, are as described for structure (I), with a compound of structure $R^1L$, in which $R^1$ is as as described for structure (I) and L is a leaving group.

Suitable leaving group L will be apparent to those skilled in the art and include for example, halogen, preferably bromine, and sulphonic acids such as p-toluene sulphonic or methane sulphonic acid.

The reaction between a polymer of structure (II) and a compound of structure $R^1L$ can be carried out in a suitable solvent at a temperature of between ambient and the reflux temperature of the solvent used. Suitable solvents included for example, a $C_{1-4}$alkanol such as methanol, dimethylformamide, tetrahydrofuran, nitromethane or sulpholane. Preferably the reaction is carried out in dimethylformamide or sulpholone at a temperature of between about 60° and 80° for a period of up to 24 hours or until the reaction is complete.

The intermediate polymers of structure (II) can be prepared from readily available materials by methods known to those skilled in the art. For example polymers of structure (II) in which X is a cross-link of structure (i) in which z is 1 and m is 2, and Z is bromine and R is methyl can be prepared by reaction of the appropriate pyridyl alkyl methacrylate, ethylene glycol bis methacrylate, and, optionally, for example, a $C_{1-20}$alkyl alkacrylate (if a comonomer unit $X^1$ is desired in the final polymer) in an aqueous suspension comprising polyvinyl alcohol in the presence of an initiator at elevated temperature. Suitable initiators will be apparent to those skilled in the art and include, for example azobisisobutyronitrile or benzoyl peroxide.

The starting monomers can be prepared by methods apparent to those skilled in the art. For example, pyridyl alkyl methacrylates can be prepared by reaction of the corresponding pyridylalkanol and methacrylic anhydride in a suitable solvent such as t-butylmethyl ether.

The polymers of structure (I) have been found to bind bile acids in in vitro models. As indicated earlier it is recognised that removal of bile acids from the intestinal tract in this way lowers serum cholesterol levels and also has a beneficial effect on protecting against atherosclerosis and its dependent clinical conditions. The present invention therefore provides in a further aspect, polymers of structure (I) for use in therapy, in particular for the lowering of serum cholesterol levels in mammals, including humans. In addition the polymers of structure (I) are expected to be of use in protecting against atherosclerosis and its sequelae, and for example, in the treatment of pruritus and diarrhoea.

When used in therapy polymers of structure (I) are in general administered in a pharmaceutical composition.

In a still further aspect of the present invention there is therefore provided a pharmaceutical composition comprising a polymer of structure (I) in association with a pharmaceutically acceptable carrier.

The compositions of the present invention can be prepared by techniques well known to those skilled in the art of pharmacy.

The polymers are preferably administered as formulations in admixture with one or more conventional pharmaceutical excipients which are physically and chemically compatible with the polymer, which are nontoxic, are without deleterious side-effects but which confer appropriate properties on the dosage form.

In general, for liquid formulations, aqueous pharmaceutically acceptable carriers such as water itself or aqueous dilute ethanol, propylene glycol, polyethylene glycol or glycerol or sorbitol solutions are preferred.

Such formulations can also include preservatives and flavouring and sweetening agents such as sucrose, fructose, invert sugar, cocoa, citric acid, ascorbic acid, fruit juices etc. In general, digestible oil or fat based carriers should be avoided or minimised as they contribute to the condition sought to be alleviated by use of the polymers. They are also subject to absorption by the polymers during prolonged contact, thus reducing the capacity of the polymer to absorb bile acids after administration.

The polymers can also be prepared as 'concentrates', for dilution prior to administration, and as formulations suitable for direct oral administration. They can be administered orally ad libitum, on a relatively continuous basis for example by dispersing the polymer in water, drinks or food, for example in a granule presentation suitable for admixture with water or other drink to provide a palatable drinking suspension.

Preferably, the polymers are administered in tablet form or in gelatin capsules containing solid particulate polymer or a non-aqueous suspension of solid polymer containing a suitable suspending agent. Suitable excipients for such formulations will be apparent to those skilled in the art and include, for example, for tablets and capsules, lactose, microcrystalline cellulose, magnesium, stearate, povidone, sodium starch, glycollate and starches; and for suspensions in capsules, polyethylene glycol, propylene glycol and colloidal silicone dioxide. If desired these dosage forms in addition optionally comprise suitable flavouring agents. Alternatively, a chewable tablet or granule presentation incorporating suitable flavouring and similar agents may be used.

Preferably the polymer is administered in unit dosage form, each dosage unit containing preferably from 0.5 g to 1.5 g of polymer.

The daily dosage regimen for an adult patient may be, for example, a total daily oral dose of between 1 and 10 g, preferably 1-5 g, the compound being administered I to 4 times a day. Suitably the compound is administered for a period of continuous therapy of one month or more sufficient to achieve the required reduction in serum cholesterol levels.

In addition the polymers of the present invention can be co-administered (together or sequentially) with further active ingredients such as HMGCoA reductase inhibitors and other hypocholesterolaemic agents, and other drugs for the treatment of cardiovascular diseases.

The following data and examples indicate the properties and preparation of the polymers of the present invention. Temperatures are recorded in degrees celsius. The exchange capacity of the ammonium substituted polymers was determined by elemental analysis and/or potentiometric titration of chloride ion. Figures quoted are expressed as milli equivalents of exchangeable chloride ion per gram of dry resin weight; and the percent cross-linking values given are based on the ratios of the starting monomers used in the polymerisation stage.

EXAMPLE 1

(a) A solution of 3-(3-pyridyl)propan-1-ol (75 g) and methacrylic anhydride (177 g) in t-butyl methyl ether (750 ml) was allowed to stand at room temperature for 72 hours. The solution was then poured into water and the organic phase washed with aqueous saturated $Na_2CO_3$ solution (5×200 ml), and 10% aqueous sodium hydroxide solution (8×200 ml). The organic solution was then dried over sodium sulphate and evaporated to dryness under reduced pressure to give 3-(3-pyridyl)-prop-1-yl methacrylate (65 g) as an oil.

3-(3-Pyridyl)propyl methacrylate (49.5 g), ethylene glycol bismethacrylate (0.5 g) azobisisobutyronitrile (1.0 g) were mixed and added to a solution of polyvinyl-alcohol (m.w. 125,000) (1 g) in distilled water (500 ml). The mixture was then stirred at 80° under an atmosphere of nitrogen, at such a rate as to maintain the monomers in suspension. After 7 hours the mixture was poured onto distilled water. The resin formed was washed by decantation with cold and hot water, filtered and washed with water, acetone and ether. Drying under reduced pressure gave an approximately 1% w/w ($\approx$1.04 molar %) cross-linked methacrylate co-polymer beads containing 4.8 meq N/g (42.89 g).

(b) The above approximately 1.04 molar % cross-linked methacrylate co-polymer (8.0 g) was suspended in tetramethylenesulphone (100 ml), methyl iodide (7 ml) was added, and the reaction heated at 60° for 20 hours. Additional methyl iodide (7 ml) was added at 4 hours. The polymer was filtered and washed with methanol and the fraction <38 $\mu$M discarded. Anion exchange was accomplished by rapidly sucking aqueous 2N sodium hydroxide (200 ml), and water (500 ml), through the polymer. The polymer was then stirred in aqueous 2N HCl:methanol (250ml:250 ml) and then allowed to stand overnight. The polymer was filtered and washed with aqueous 2N HCl, water, methanol and ether and finally dried under vacuum to give a cross-linked 3-(N-methyl-3-pyridinio)propyl methacrylate chloride co-polymer (7.83 g, 3.15 meq $Cl^-$/g).

EXAMPLE 2

The above approximately 1.04 molar % cross-linked 3-(3-pyridyl)propylmethacrylate co-polymer (Example 1) (6.0 g) was suspended in tetramethylenesulphone (80 ml), 1-bromooctane (15 g) was added, and the reaction heated at 60° for 20 hours. The polymer was filtered and washed with methanol and the fraction <38 $\mu$M discarded. Anion exchange was accomplished as in Example 1(c) to give a cross-linked 3-(N-octyl-3-pyridinio)-propyl methacrylate chloride co-polymer (8.5 g, exchange capacity 2.50 meq $Cl^-$/g).

EXAMPLE 3

The above approximately 1.04 molar % cross-linked 3-(3-pyridyl)propylmethacrylate co-polymer (Example 1a) (6.0 g) was suspended in tetramethylenesulphone (80 ml), 1-iodododeoane (26 g) was added, and the reaction heated at 60° for 20 hours. The polymer was filtered and washed with methanol and the fraction <38 $\mu$M discarded. Anion exchange was accomplished as in Example 68 to give a cross-linked 3-(N-dodecyl-3-pyridinio)-propyl methacrylate chloride co-polymer (9.03 g, exchange capacity 2.02 meq $Cl^-$/g).

EXAMPLE A

A chewable tablet composition can be prepared from the following:

|  | mg/tablet |
| --- | --- |
| Compound of Structure 1: | 1250 |
| Silicon dioxide | 15 |
| Microcrystalline cellulose | 280 |
| Sorbitol | 445 |
| Lactose | 450 |
| Sweetener | 5 |
| Peppermint | 30 |

| | mg/tablet |
|---|---|
| Magnesium Stearate | 25 |
| | 2500 mg |

EXAMPLE B

A food additive composition, for example, a sachet for reconstitution or mixing with food, is prepared by incorporating into a powder formulation compound of structure (I) (250 mg), sodium carboxymethylcellulose (50 mg), sucrose (2400 mg) and flavours (50 mg).

DATA

In vitro Dissociation assay

The following assay provides a measure of affinity of the polymers of the invention for the bile acid, glycocholrate (GC) based on the amount of GC bound at a subsaturating concentration of 5 mM (t=0), and an estimate of the rate at which this bile acid dissociates into a large volume of buffer. The results are obtained as initial amounts of GC bound (t=0) and amounts remaining bound after 2 minutes in buffer (t=2min); from these figures the % dissociation i.e. the proportion of bound GC dissociated from the polymer after 2 minutes can be obtained. The lower the % dissociation the more efficient the polymer can be expected to be in extracting bile acids in vivo.

Method

Test compound (150 mg) was equilibrated with 5 mM sodium glycocholate (30 ml) in Krebs' buffer. The compound was separated by centrifugation and the total bound determined by subtraction of the amount in the supernatant from the total bile acid used. Dissociation was measured by resuspending the compound in Krebs, buffer, shaking and sampling the mixture through a filter at several time points up to 20 minutes. Radioactivity and hence bile acid dissociated was determined in the filtrate.

RESULTS

The following % dissociation figures were obtained:

| Examples | % Dissociation |
|---|---|
| 1 | 72 |
| 2 | 27 |
| 3 | 8 |

What is claimed is:

1. A polymer of structure (I)

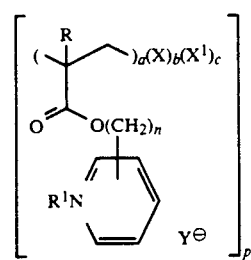

in which
a, b and c indicate the relative molar percentages of the units present in the polymer, (a) being from about 25 to about 99.5 molar percent, and (b) being from about 0.5 to about 8 molar percent;
X is a cross-linking unit;
$X^1$ is a stryene, an alkyl alkylate of structure (ii) or an alkylstyrene of structure (iii)

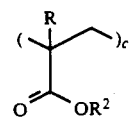

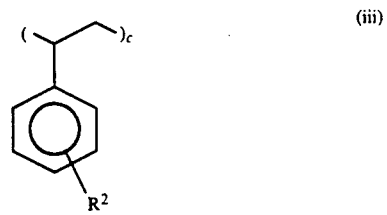

in which R and c are as described above and $R^2$ is $C_{1-20}$alkyl;
R is hydrogen or $C_{1-4}$alkyl;
$R^1$ is $C_{1-20}$alkyl or $C_{1-20}$aralkyl;
n is 1 to 20.
p is a number indicating the degree of polymerisation of the polymer; and
$Y^-$ is a physiologically acceptable counter ion.

2. A polymer as claimed in claim 1 in which (b) is a cross-linking unit of structure (i):

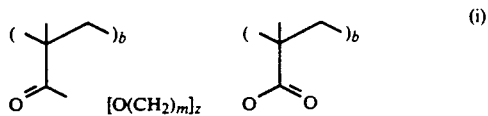

in which m is 2 to 6 and z is 1 to 4.

3. A polymer as claimed in claim 2 in which z is 1 and m is 2.

4. A pharmaceutical composition comprising a polymer of structure (I) as claimed in claim 1, in association with a pharmaceutically acceptable carrier.

5. A method of lowering serum cholesterol levels which comprises administering to a subject in need thereof an effective amount of a polymer of structure (I) as claimed in claim 1.

* * * * *